United States Patent
Richards

(10) Patent No.: US 10,995,063 B2
(45) Date of Patent: May 4, 2021

(54) INTEGRATED PROCESSING SYSTEM WITH CONTINUOUS ACID LOOP FOR CONVERTING METHANE TO METHANE-SULFONIC ACID

(71) Applicant: Veolia North America Regeneration Services, LLC, Houston, TX (US)

(72) Inventor: Alan K. Richards, Palm City, FL (US)

(73) Assignee: Veolia North America Regeneration Services, LLC, Houston, TX (US)

( * ) Notice: Subject to any disclaimer, the term of this patent is extended or adjusted under 35 U.S.C. 154(b) by 0 days.

(21) Appl. No.: 15/917,631

(22) Filed: Mar. 10, 2018

(65) Prior Publication Data
US 2020/0095197 A1      Mar. 26, 2020

Related U.S. Application Data

(60) Provisional application No. 62/601,065, filed on Mar. 10, 2017.

(51) Int. Cl.
| | | |
|---|---|---|
| C07C 303/02 | (2006.01) | |
| B01J 19/00 | (2006.01) | |
| C07C 309/04 | (2006.01) | |

(52) U.S. Cl.
CPC ......... *C07C 303/02* (2013.01); *B01J 19/0046* (2013.01); *B01J 2219/00033* (2013.01); *C07C 309/04* (2013.01)

(58) Field of Classification Search
CPC ... C07C 303/02; C07C 309/04; B01J 19/0046
USPC .......................................................... 560/30
See application file for complete search history.

(56) References Cited

U.S. PATENT DOCUMENTS

2008/0161591 A1   7/2008   Richards
2016/0289181 A1   10/2016  Ott et al.

*Primary Examiner* — Deborah D Carr
(74) *Attorney, Agent, or Firm* — Dunlap Codding, P.C.

(57) ABSTRACT

Methods and machinery are described for combining methane with sulfur trioxide to make MSA, in a system that sustains optimal concentrations of reactants in the main reactor for high yields, efficiency, and profitability. Rather than simply making MSA and then removing it, this design uses a "continuous loop system" with: (i) a "rich acid" stream containing a high concentration of MSA, mixed with sulfuric acid, which will emerge from the main reactor, and (ii) a "reduced acid" stream containing a low concentration of MSA (still mixed with sulfuric acid), from an extractor unit (such as a distillation unit) which removes some but not all of the MSA from the "rich acid". Additional subassemblies are described which enable the main reactor to work efficiently, at a sustained high flow-through capacity. This system also can be scaled up or down, for any daily MSA production rate.

7 Claims, 1 Drawing Sheet

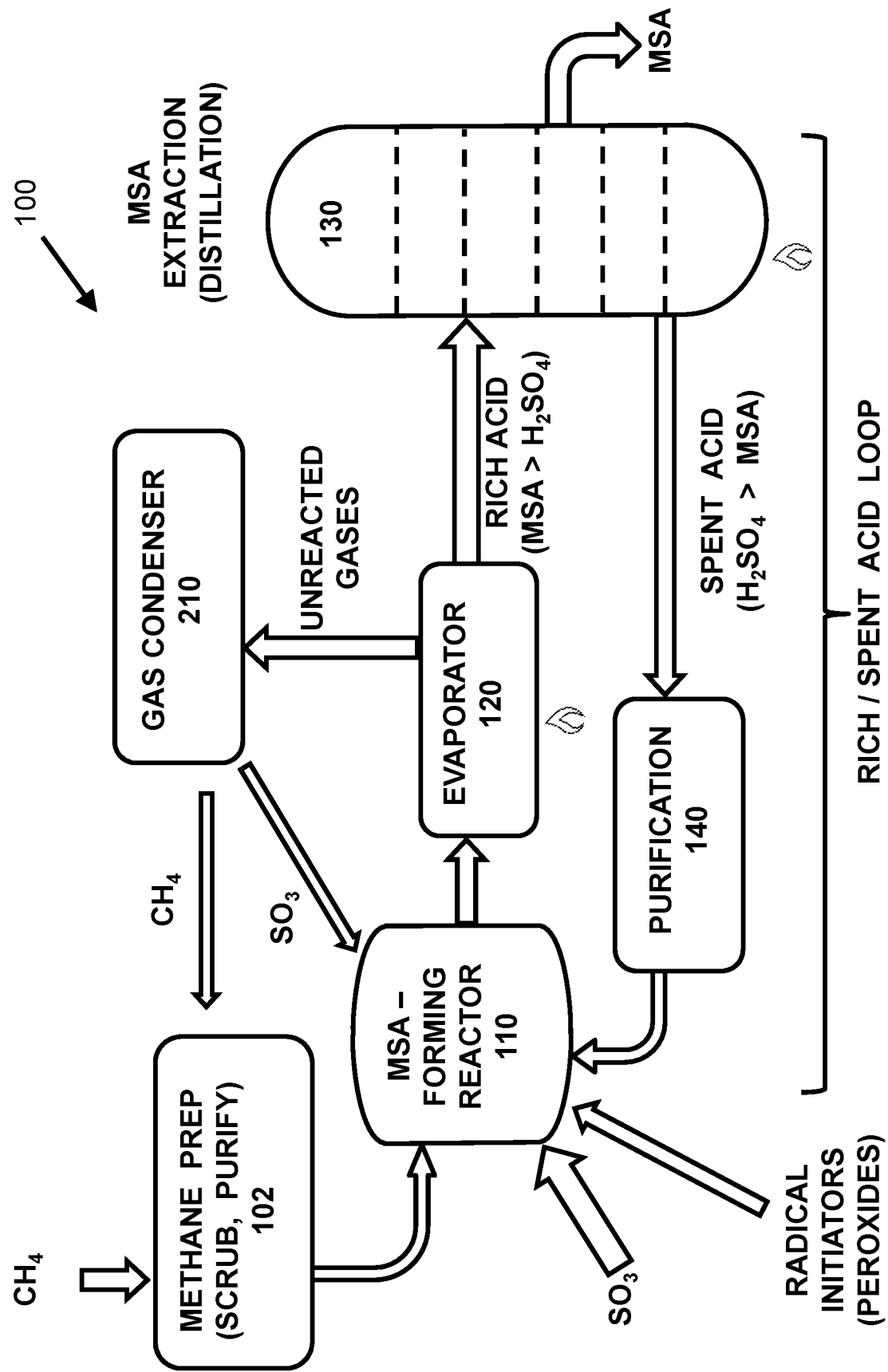

INTEGRATED PROCESSING SYSTEM WITH CONTINUOUS ACID LOOP FOR CONVERTING METHANE TO METHANE-SULFONIC ACID

RELATED APPLICATION

This application claims a priority date under 35 USC 119, based on provisional application 62/601,065, filed on Mar. 10, 2017.

BACKGROUND

This invention is in the fields of organic chemistry and chemical engineering. In specific, it relates to a method and equipment for combining methane gas and sulfur trioxide to form methane-sulfonic acid (MSA), a valuable commodity chemical used in the electronic, metal-processing, and chemical industries.

A method for converting methane gas into MSA, rapidly and with high selectivity and yield, is described in several published US patent applications and Patent Cooperation Treaty (PCT) applications. U.S. Pat. No. 7,282,603 and PCT application WO 2004/041399 describes the use of a "radical initiator" to initiate a chain reaction, which will bond methane (normally a gas, with the formula CH4; for simplicity and search purposes, subscript fonts are not used in chemical formulas herein) to sulfur trioxide (SO3) to make MSA (the phrase "methane-sulfonic acid", either with or without a hyphen, is the standard industry name for this compound, even though the phrase methyl-sulfonic acid is more chemically accurate). That chain reaction is initiated by using any of various known methods (such as controlled usage of special types of peroxide compounds) to remove an entire hydrogen atom (both a proton and an electron) from methane. This generates aggressively reactive methyl "radicals" having unpaired electrons, indicated as H3C*, where the asterisk indicates an (aggressively reactive) unpaired electron. Under proper conditions inside an MSA-forming reactor, the methyl radicals will attach themselves to SO3, thereby forming an incomplete and unstable radical version of MSA. An MSA radical has the right combination of strength and instability to enable it to take a hydrogen atom away from a molecule of fresh methane, thereby creating both: (i) stable MSA, in liquid form, and (ii) a new methyl radical, which is exactly what is needed to keep the chain reaction going, so long as fresh methane and fresh SO3 continue to be pumped (at high pressure) into the MSA-forming reactor.

Applicant's PCT application PCT/US2004/019977, published as WO 2005/069751, depicts a number of ways to initiate that radical chain reaction, by converting stable methane, CH4, into methyl radicals, written herein as H3C*. That assortment of methods is not exhaustive; instead, it is intended mainly to point out and illustrate that chemists do indeed know how to create methyl radicals, which form a crucial "activating" or "triggering" compound which, if properly handled, can set in motion a "radical chain reaction" which, under proper conditions, can keep going for a large number of cycles.

Although any of several known routes can be used to convert methane into methyl radicals, one of the most desirable for generating relatively large quantities of methyl radicals for large-scale chemical manufacturing operations uses specialized peroxide compounds. By definition, a "peroxide bond" has two oxygen atoms, bonded directly to each other; this can be written generically as X—O—O—Y. Two sulfur-containing peroxides, referred to by the common names "Caro's acid" and "Marshall's acid", are good for generating methyl radicals, and another compound of interest for such use is called "di-methyl-sulfonyl peroxide", abbreviated as DMSP. It is similar to Marshall's acid, except with a methyl group (rather than the hydroxy group) attached to each of the two "ends" of the symmetric peroxide. It can be manufactured directly, by simply passing MSA through an electrolysis unit.

Accordingly, the combination of methane with sulfur trioxide creates the compound MSA in a balanced reaction as follows:

This radical-initiated chain reaction is described in U.S. Pat. No. 7,282,603 and in PCT applications WO 2004/041399 and 2005/069751.

The foregoing Background information leads to an important point: by using this recently-discovered reaction, it is possible to convert methane gas into MSA, in a way which can lead to good and high yields of a relatively pure high-value chemical product, through a specialized process which uses a radical chain reaction.

In all prior published descriptions of this chemical discovery by the Applicant herein, a general working assumption applied, which pointed strongly toward the belief that, in order to work effectively and efficiently, the reaction mixture should be kept as clean, simple, stripped-down, uncluttered, and uncomplicated as possible, and it should contain nothing except the essential components.

That assumption arose partly from its manner of discovery, which occurred when the Inventor realized that a somewhat similar reaction, described years earlier by other researchers in the prior art (Basickes et al 1996), could and should be changed and altered, in ways that simplified and uncluttered the reaction by removing certain other atomic species that prevented the radical-initiated chain reaction from being useful for large-scale industrial operations. Since a major improvement in that earlier published reaction arose by simplifying it, and stripping it down to the minimum essential ingredients, that insight set the tone and course for the research which followed over a span of multiple years.

Furthermore, that guiding assumption was entirely consistent with the nature of how molecular radicals, and radical reactions, work. As suggested by the very term, "radicals" are highly unstable and aggressively reactive, and most types of "radicals" (i.e., a chemical species which has a so-called "unpaired electron") will chemically attack, react with, and damage, nearly any type of molecule. Therefore, the basic "theory of the reaction" discovered by the Inventor was that steps had to be taken to eliminate any other candidate species, which might allow any radical within the reaction mixture to do anything other than undergoing a single, specific, tightly-constrained next step in a tightly limited, narrow, "tunnel-shaped" reaction pathway. Accordingly, that goal was assumed to be directly undercut, if any other non-essential molecular species were allowed to exist in the reaction mixture.

However, despite the foregoing, it eventually was realized that, while the "hyper-simple, nothing except absolutely essential components" radical chain reaction can indeed work and function exactly as claimed, it is nevertheless not the best, most efficient way to convert large quantities of methane, to MSA, in a commercial-scale industrial reaction.

During research efforts to scale up the methane-to-MSA chain reaction to commercial scales, it became apparent that certain "chain-terminating" species were gradually accumulating inside any reactor which was being used to carry out the reaction, regardless of the levels of care and effort that were being made to prevent the formation of those "chain-terminating" species. As described elsewhere, and as understood to chemists, the yields, outputs, and profitability of any industrial-scale chemical reaction which requires and depends upon a "chain reaction", can and will be badly damaged, reduced, and impaired, if and when "chain terminating" molecular species begin to occur and accumulate, inside any reactor which is attempting to keep such a chain reaction running continuously, with the best possible yields. Indeed, the very nature of the phrase, "chain terminating", clearly indicates that any such molecular species can bring a desired and productive chemical reaction to a halt. Therefore, if it is impossible to prevent the creation of "chain terminating" species in some particular chemical chain reaction, then it becomes necessary to figure out some way to "quench" (or neutralize, inactivate, deactivate, or similar terms) whatever species has been found to be the "chain terminating" species that is stopping and blocking the desired chain reaction.

In the particular case involving the conversion of methane gas into MSA by a radical chain reaction, the most important (by far) terminating species was recognized, after long and extensive efforts, as sulfur dioxide (SO2). Since it is currently believed (under the current state of the art) to be effectively impossible to completely prevent the formation of some quantity of chain-terminating SO2 molecules inside a reactor that is using SO3 to convert methane to MSA, the focus of the Applicant's research was thereby obliged to shift somewhat. Instead of trying to prevent the formation of SO2, the Applicant began focusing on ways to quench it, and neutralize it, by converting any such SO2 into some other, different, non-chain-terminating species.

As described and claimed in more detail in a separate patent application that is being filed simultaneously with this application, that research culminated in the realization that a mixture of at least two or more different sulfur-containing peroxide compounds can indeed accomplish both of two goals, which are (i) triggering the desired radical chain reaction, at high and efficient levels; and, (ii) oxidizing any SO2 that occurs inside the reactor, to convert it into SO3, which is the desired species that helps the reaction continue.

However, that discovery has forced the adoption and use of other accommodating changes in the overall processing system. Accordingly, a new and different approach to designing an optimized and profitable systematic and integrated processing system, for converting methane into MSA, has been developed, as described herein.

Furthermore, once that new approach was settled upon, it was realized that, with certain additional enhancements, it became possible to make it highly "scalable" (i.e., it can be "sized" to handle any daily production rate of MSA that is desired, depending on the availability and flow rates of a methane stream and SO3 supplies that are available at that production site). In addition, this type of processing system design can be adapted to enable it to handle methane streams having a wide range of chemical contents, ranging from "sour gas" (i.e., methane gas with significant sulfur content and an unpleasant odor) to "sweet gas" (methane with no sulfur and no odor), as well as methane streams having widely varying concentrations of other gaseous components (such as carbon dioxide).

Accordingly, one object of this invention is to disclose improved processing methods, processing components, and processing subassemblies that can handle combinations of liquids and gases (at elevated but not extreme temperatures and pressures), which can be assembled into a complete and integrated processing system for optimally efficient and high-yield conversion of methane, into methane-sulfonic acid (MSA).

Another object of this invention is to disclose a complete and integrated processing system, which is designed and suited for efficiently and rapidly combining methane gas and sulfur trioxide to make MSA as a high value, end-use compound, and which is specifically designed to be "scalable" across a very wide range of MSA production rates, so that different versions of this processing system can be either "scaled up" or "scaled down" for the desired production rate at any particular site.

Those and other objects of the invention will become more apparent through the following summary, drawings, and detailed description.

SUMMARY OF INVENTION

This application describes an improved method or process for combining methane with sulfur trioxide to make MSA, in an integrated processing system which: (i) is designed to efficiently and optimally handle a mixture of radical initiator compounds, sulfuric acid, chain-terminating compounds such as SO2, and other non-essential compounds inside the system; (ii) is designed to sustain optimal concentrations of reactants in the MSA-forming reactor for high reaction rates, efficiency, and profitability for the production of MSA; and, (iii) can be scaled up or down for any daily MSA production rate. Rather than simply making MSA (by combining methane with SO3, using a radical chain reaction) and then removing that MSA from the system, this improved processor design uses "continuous loop system" which handles both: (i) a "rich acid" stream which contains a relatively high concentration of MSA (which normally will be mixed with sulfuric acid), which will emerge from the MSA-forming reactor vessel, and (ii) a "reduced acid" stream which contains a relatively low concentration of MSA (still mixed with sulfuric acid), which will emerge from an "extraction processor" (such as a distillation unit) which removes some but not all of the MSA from the "rich acid" stream. In order to enable those two main components of the reactor system (i.e., the MSA-forming reactor, and the MSA extraction processor) to function optimally in a continuous flow mode, various other items of processing equipment, with each one designed to carry out one or more specific supporting functions, also should be incorporated into the overall processing system.

In addition, this integrated system is intentionally designed to remove substantial quantities of unreacted methane and SO4 (mixed in with the "rich acid" mixture of MSA and sulfuric acid) from the MSA-forming reactor. By using an evaporator unit, it will then extract and remove the unreacted methane and SO3 components from the rich acid stream, before the rich acid stream is sent to the MSA extractor, and it will return the unreacted methane and SO3 streams, back into the MSA-forming reactor. This can enable the MSA-forming reactor to work in an efficient and economical manner, by allowing it to work at a sustained "peak flow-through capacity" while relieving it of any necessity to keep a reaction running after the concentrations of reagents have dropped into a "low yield" efficiency zone in an "asymptotic" reaction that will never reach 100% completion. Stated in other words, this system is designed to constantly provide a recirculating, steady-state surplus and over-supply of methane and SO3, inside the MSA-forming reactor, since those conditions will enable an MSA-forming reactor to operate at maximal daily production rates, for maximum profitability and economic results.

BRIEF DESCRIPTION OF THE DRAWING

FIG. 1 is a schematic drawing which depicts the main processing vessels in an MSA manufacturing system.

DETAILED DESCRIPTION

As briefly summarized above, this application discloses and describes an improved type of integrated processing system, for combining methane gas with sulfur trioxide to make a compound called methane-sulfonic acid (MSA). To organize this description in a logical manner, subheadings are used below to identify and discuss the major components of this integrated processing system. The entire system is referred to by callout number 100, in FIG. 1, with the main processing devices having their own callout numbers.

In FIG. 1, "open" arrows are used to depict the piping components which will transfer gaseous and/or liquid mixtures or components from one processing vessel to another, with an arrowhead depicting the direction of flow in any such pipe. In general, because these pipes will be handling strongly acidic and corrosive compounds, they must be made of very expensive alloys which have exceptionally high levels of resistance to chemicals and corrosion, preferably with internal coatings (such as poly-tetra-fluoro-ethylene, commonly known as TEFLON™) to further increase their design lives.

Because of corrosion factors (and in accord with conventional chemical engineering design principles), not just one but two independently-operable valves should be installed at each inlet or outlet pipe, adjacent to any reactor. The "outer" valve (i.e., the valve which is farther away from the reactor, in any pair of valves, which can also be called a "distal" valve or similar terms) will be used for flow control during all normal operations, while the "inner" or "proximal" valve (i.e., the valve which is closer to the reactor) normally is left fully open at all times, except during emergencies, or when a worn or corroded "distal" valve needs to be repaired or replaced. The presence of an "inner" valve, which is never used except when specifically needed, makes it simpler, faster, and easier to replace an "outer" valve or any portion thereof, whenever a need arises, without having to drain out the contents of a reactor vessel.

In FIG. 1, a small depiction of a flame is used to indicate that a heat input can be used, at or near that location, to enable (or speed up, or render more efficient) a processing step. For example, evaporator unit 120 can be heated (and also subjected to a vacuum), to increase the extent to which unreacted gases will be removed from the "rich acid" stream that emerges from MSA-forming reactor 110; similarly, if a distillation column 130 is used to extract MSA from the "rich acid" stream, it likely will need to be heated. By contrast, since the radical chain reaction inside MSA-forming reactor 110 will be an exothermic reaction which will generate its own heat, it is more likely to require cooling, than heating, at any operating sites which handle moderate to large flow rates. For different reasons, gas condenser 210 also is likely to require cooling, rather than heating.

Methane Preparation Unit 102

In any location where a methane-to-MSA manufacturing facility will operate, the "quality" of the methane stream will be known, and must be taken into account. In this context, "quality" encompasses and refers to the concentrations of impurities in the methane stream at that particular location. Such impurities often include various combinations of sulfur (usually in the form of hydrogen sulfide, a toxic and foul-smelling gas); carbon dioxide; ethane or propane (these are larger hydrocarbons which have higher energy content and value than methane; they can be extracted and sold as valuable products in their own right); certain types of acidic impurities; and various other minor impurities. Methods for removing any or all such impurities from a methane stream are standard, conventional, and well-known aspects of gas treatment, and those skilled in that art can select any particular type of gas pre-treating process which is deemed to be useful and economic, in preparing and pre-treating any methane stream which will be processed in an MSA-forming reactor.

Accordingly, a methane preparation unit 102 is shown in FIG. 1, as a "gateway" device which will be used to process (in any manner that is deemed to be necessary, at any particular methane conversion site) both: (i) the newly-arriving methane which will be converted into MSA, and (ii) any unreacted methane gas which has been recovered (via an evaporator unit 120, and a gas condenser unit 210) from the "rich acid" output stream that emerges from the MSA-forming reactor 110.

MSA-Forming Reactor 110

The MSA-forming reactor vessel 110 as shown in FIG. 1 should operate at high pressure, to speed up its ability to forcibly drive the absorption of methane gas into the liquid reagents and solvents inside the vessel. The reagents which will be pumped into reactor 110 include:

(i) methane, as both a large stream of "fresh" methane, and a smaller stream of recycled unreacted methane which has passed through evaporator 120 and condenser 210 (and which can also be passed through methane preparation unit 102, if desired):

(ii) sulfur trioxide (SO3), as a combination of both (a) a "fresh stream" (which must generally be equal, in input rates, to the quantity of SO3 which is removed from the system as part of the MSA product), and (b) a recycle stream which has passed through evaporator 120 and condenser 210, which will remain inside the system to help it keep running at maximal efficiency; and, (iii) one or more "radical initiators", which in most cases will be sulfur-containing peroxide compounds. As described elsewhere, the bond which couples two oxygen atoms to each other, in a peroxide compound, can be broken in a controllable manner, by means such as heat, ultraviolet radiation, or a "tuned" laser beam. That cleavage will release two oxygen radicals, and at least one of those radicals, in a properly selected "radical initiator" which will be suited for use in this particular setting, must have enough strength to rapidly and efficiently remove an entire hydrogen atom (both the proton, and the electron) from a molecule of methane, in a manner which creates a methyl radical (written herein as H3C*, where the asterisk represents an unpaired electron).

In a properly-functioning MSA-forming reactor, newly-formed methyl radicals will attach themselves to SO3 molecules, thereby creating "MSA radicals". Those MSA radicals have enough strength to attack another molecule of methane, and remove one of its hydrogen atoms, thereby creating a new methyl radical, which will then attach itself to another SO3 molecule, thereby creating another MSA radical. This is the "radical chain reaction" which causes methane and SO3 to bond together, not in multiple possible configurations (which would generate an unwanted mixture of products and byproducts), but in a consistent, reliable, uniform manner, which creates MSA (the desired product) with good yields, and high purity.

Accordingly, at least one sulfur-containing peroxide which is suited as a "radical initiator" for this use can be used to initiate the MSA-forming radical chain reaction, and provisions can be made to inject that type of radical initiator into the MSA-forming reactor. For example, the peroxide compound can be pumped (at high pressure) through a segment of tubing which has a "window" segment made of a clear and chemical-resistant plastic, polymer, or glass material. The ultraviolet or laser light will pass through the clear window and "hit" the peroxide compound in a manner which will break the peroxide bond, thereby releasing unstable (or "activated") radical species just as the peroxide/radical compound is entering the MSA-forming reactor. Alternately, in some cases, it may be preferable to inject a chosen peroxide compound into the reactor, and allow the heat inside the reactor to become the "activating agent" which will break the peroxide bond, and release the radical species in an "in situ" activation step.

Because of reaction kinetics, yield and economic factors, and the problems that are caused by "chain terminating" species that can be created inside the reactor (notably including sulfur DI-oxide, SO2), in most cases it will be preferable (or even necessary) to either continuously or intermittently inject additional quantities of one or more radical initiators, into the MSA-forming reactor 110.

In addition, it should be mentioned that other work by the same Applicant herein has indicated that, in at least some situations, it may be preferable to inject (either continuously, or intermittently) a mixture of (or a cycling pattern which includes) two or more different peroxide compounds, including (a) at least one first peroxide compound which is intended mainly to start up new radical chain reactions, and (b) a second peroxide compound which is intended mainly to "quench" and eliminate any molecules of SO2, which has been identified as an most important "chain terminating" species.

Good candidates for use as the first peroxide compound (i.e., to simply initiate the chain reaction) include:

(i) a compound called "Marshall's acid", which is a symmetric peroxide which effectively has two identical sulfuric acid radicals, attached to each other via a peroxide bond; its chemical formula can be written as HOS(O2)O—OS(O2)OH, or as H2S2O8;

(ii) "methyl-Marshall's acid", which is Marshall's acid with a single methyl group bonded to one of the sulfuric groups; it is somewhat more stable and easy to handle and use, compared to Marshall's acid; and, (iii) di-methyl-sulfonyl peroxide (abbreviated as DMSP), which also can be called "di-methyl-Marshall's acid", since it has two methyl groups added to Marshall's acid (one at each end). As described elsewhere, DMSP can be formed by simple electrolysis of MSA; therefore, a convenient way to provide DMSP, if it is chosen for use as an initiator, would be to simply take a small portion of the MSA final product stream (which is shown as emerging from extraction unit 130, in FIG. 1), and pass it through an electrolysis unit at the MSA manufacturing site.

The list above is not exhaustive, and other non-symmetric peroxide compounds can be used, such as a compound called Caro's acid (peroxy-mono-sulfuric acid, HOS(O2)O—OH). When Caro's acid is split, it will release one sulfuric radical which is useful for starting the chain reaction; however, the other radical will simply be a hydroxy radical, which does not have enough strength to initiate a chain reaction.

However, Caro's acid, and a compound which can be called methyl-Caro's acid (with the formula H3C—S(O2)O—OH) may be very useful as a second initiator compound, which is intended mainly not to start the chain reactions, but to "quench" and eliminate any sulfur DI-oxide (SO2) which has accumulated inside the MSA-forming reactor. As described in more detail in a separate simultaneously-filed application, methyl-Caro's acid (and Caro's acid) are very potent oxidizing agents, and the hydroxy radicals which they will release can help to rapidly and efficiently oxidize and convert SO2 (the unwanted chain-terminating disruptor) into SO3 (i.e., the normal and desired reagent for MSA formation). Therefore, as described in more detail in a separate simultaneously-filed application, methyl-Caro's acid (and possibly Caro's acid) offer good candidate for use as a "second" peroxide compound in a mixture or combination of peroxides which can both (i) start the chain reactions, and (ii) help keep the chain reactions going, for as many cycles as possible, inside the MSA-forming reactor.

As another point concerning the reagents that will be pumped into the MSA-forming reactor 110 as shown in FIG. 1, care should be taken to ensure that, as SO3 is being pumped into the reactor, as much of the SO3 as possible should be in the so-called "gamma" form. As illustrated in the Wikipedia entry on sulfur trioxide, the "gamma" form is a "trimer" in which 3 molecules of SO3 cluster together, to form a semi-stable cluster that can be broken apart fairly easily, allowing the individual SO3 molecules to react readily with other reagents. Over time, and especially when non-optimal storage conditions arise, the small "gamma" clusters will agglomerate into "alpha" and "beta" forms, which are larger, and harder to break apart; this makes it more difficult for the alpha and beta forms of SO3 to react with other molecules. Accordingly, proper handling and usage of sulfur trioxide is itself a specialized field of art, and anyone wishing to run an MSA manufacturing facility as described herein needs to be aware of that field of art, and should approach it with the help of someone who is skilled and experienced in that particular art.

One approach which makes it easier to work with and keep SO3 in the desired "gamma" form involves keeping it dissolved in sulfuric acid, as a solvent. The most common forms of purified SO3 sold today are not pure SO3, but instead, are mixtures of SO3 in sulfuric acid. That mixture is called "oleum", regardless of the relative contents of the SO3 and the sulfuric acid solvent, and anyone who wishes to purchase oleum must specify which particular concentration of SO3 s/he wants, in that particular oleum mixture.

Accordingly, when the "gamma" SO3 and oleum factors are considered, and when the need for not just one but at least two different radical initiators (one to initiate chain reactions, and one to quench and convert unwanted SO2 molecules into SO3) are taken into account, the invention and the system design herein simply accepts that highly concentrated sulfuric acid can and must be used as a major component of the solvent liquid which will circulate through the system, in an MSA manufacturing system as described herein. This clearly will require that all vessels, piping, and handling components which will come into contact with any sulfuric acid must be made of highly specialized alloys (preferably with protective coatings) that have been specifically designed and selected for handling concentrated sulfuric acid.

The comment above, stating that, "sulfuric acid can and must be used as a major component of the solvent liquid", reflects the fact that the MSA itself will also serve as one of the "solvents" in this manufacturing system, and is not just the product. The methyl group which forms one of the two major domains of MSA forms an "oleophilic" substituent, which actively helps methane gas become adsorbed, into a liquid mixture which contains MSA. This is one of the features and advantages which can help this system run efficiently, as it uses high pressure to help drive and force a gaseous compound into a liquid mixture.

Preferred temperature ranges, for operating the MSA-forming reactor 110, usually will be about 40 to 90 C, unless and until results in continuous-flow pilot plants indicate otherwise. The minimal pressure range, for small systems, usually will be at least about 40 bar (i.e., 40 times standard barometric pressure); for larger systems, pressures may exceed 100 bar, since higher pressures generally will cause methane gas to become dissolved into a liquid reaction mixture more rapidly.

As a final comment concerning the MSA-forming reactor 110, it should be recognized that one of the more important insights which has led to this current invention is that it is not advisable (for economic reasons) to try to run reactor 110 in a way which is (or under conditions which are) managed and intended to generate a high percentage yield of methane-to-MSA conversion, on each and every "pass" that methane takes through the reactor 110. The reason for this arises from the fact that the methane-to-MSA conversion process depends directly on an individual molecule of methane, being converted into an individual methyl radical, which will then attach itself to a an individual molecule of SO3, in a way which creates an MSA radical, will then become a single molecule of complete and stable MSA. Under those conditions, as the reaction proceeds toward completion, the numbers and concentrations of unreacted methane and SO3 molecules will rapidly drop, as a direct, inevitable, and necessary result of most of them being already consumed and altered by the reaction. Under those conditions, it will take longer and longer for any "lonely" methyl radicals to find fresh SO3 molecules that have not already been converted into MSA. This reaction therefore becomes, in effect, what can be called an "asymptotic" reaction, which can never reach all the way to completion.

As a visual analogy, one can think of an "asymptotic curve" plotted on a graph. This phrase refers to a curve that will forever continue to get closer and closer to some final value, but will never actually reach that final value. The simplest example is this type of curve can be seen in a graph of "y=1/x", where y—the vertical value—will keep getting smaller and smaller, and closer to absolute zero, as X keeps climbing higher and higher, up into the hundreds, then thousands, then millions, then billions, and on and on, forever. In that graph, no matter how close Y gets to absolute zero, it can never reach actual, absolute zero. That makes it an "asymptotic" curve.

In a similar manner, no MSA-forming reaction, inside a real-world reactor, will ever reach absolute 100% completion, where the last lonely methyl radical was able to find, somehow, the last molecule of fresh unreacted SO3. Instead, this type of radical chain reaction (when expressed in appropriate terms, such as tons of MSA formed, per hour) will run much more efficiently and profitably, if surpluses of both unreacted methane, and unreacted SO3, are maintained continually, inside the reactor.

That factor leads to and explains the presence of evaporator unit 120, and gas condenser 210, in FIG. 1, as discussed below.

Evaporator Unit 120 and Gas Condenser 210

As described above, the MSA-forming reactor 110 can be operated most efficiently and productively, by designing the radical chain reaction to run with constant and sustained surpluses of both unreacted methane, and unreacted SO3, presumably at all times (except during cleanout and maintenance). Since those will be the operating conditions inside the reactor 110, the initial "rich acid" stream which emerges from the MSA-forming reactor 110 will necessarily contain substantial quantities of unreacted methane (as a heated gas that will be "entrained" in the hot liquid output stream), and unreacted SO3.

To remove those unreacted components from the initial "rich acid" stream, they are passed through one or more devices, subassemblies, and processes, which are grouped together and collectively referred to as "evaporator 120" in FIG. 1. These components can include, for example, two or more pressure reducers which act in a sequential manner, such as:

(i) an initial device or subassembly which is not heated or subjected to a vacuum, and which can be called a pressure reduction valve, a "flash" or "flashing" unit, or similar terms, and which will allow a large and rapid reduction in pressure, from the very high pressure levels of reactor 110, down to atmospheric levels (or at least to levels which are much closer to atmospheric levels, than to the high pressure levels inside reactor 110); and, (ii) a "second stage" components or set of components, which can use either or both of: (i) active heating, and/or, (ii) a suction pump to create vacuum conditions (i.e., less than atmospheric pressure), inside that component or chamber, to further drive and enable removal of unreacted methane and SO3 from the rich acid stream.

These devices, working collectively in "evaporator 120" device or subassembly, will enable the unreacted methane (which is a very light, thin, volatile gas, under any normal or near-normal conditions) and SO3 (which is also likely to pass through a gaseous "flashing" phase, due to the heat of the acid stream, and due to interactions with methane molecules escaping from the hot liquid) to be separated from the liquid "rich acid" stream.

Regardless of the specific evaporator components or conditions that have been chosen, tested, and optimized at any specific location, a generally gaseous stream (which may contain some liquid content) containing large percentages of any unreacted methane and unreacted SO3 which were initially dissolved in the "rich acid" liquid that emerged from reactor 110, can and will be pulled out of evaporator 120.

That gaseous stream can be passed through a gas condenser unit 120, if desired, to separate the methane component from the SO3 component, and to handle any additional compounds that became entrained in the output stream from evaporator 120. If this approach is used, all or any portion of the separated methane stream which emerges from gas condenser unit 120 can be passed through any scrubbing, purifying, or other methane preparing unit or subassembly 102 which is being used at that location.

Alternately, in some locations, the owners may decide to not incorporate or not use a gas condenser 210, and can pump any unreacted methane and SO3 which have emerged from evaporator 120, directly back into the MSA-forming reactor 110.

MSA Extraction Processor 130

The "rich acid" which emerges from evaporator 120 (after unreacted CH4 and SO3 have been removed) is then send to an "MSA extraction unit" 130, as illustrated on the right side of FIG. 1.

This extraction unit will be designed, quite simply, to remove (or extract, withdraw, isolate, or similar terms) MSA (in a relatively pure form, with little or no sulfuric acid or any other impurities remaining in it), so that the MSA can be sold and shipped, as a final product. In some situations, a single extraction unit which can achieve some targeted level of purity (such as 99% or higher) may be preferred, and the final product will be MSA with a purity level of, for example, 98% for some batches which can be sold at a first relatively low price, and 99% for other batches which can be sold at a higher price (comparable to premium gasolines, motor oils, and other chemical products). In other situations, an initial extraction unit will be the first of two or more purification units, and any MSA which emerges from it with known purity level (such as 95% or higher) can then be sent to a "finishing" (or polishing, or similar terms) unit, which can further purify the semi-pure MSA to an exquisitely highly level of purity, for output products that are intended for extremely sensitive usage (such as for the manufacture of extremely sensitive and valuable semi-conductor wafers and components, which is one of the more important and valuable uses for MSA), and which therefore can command higher prices than less pure, lower-grade MSA preparations used for things like bulk processing of lead.

When applied any single chemical operation, the term "purified" is used broadly, and does not require or refer to any absolute level or standard of purity. Accordingly, an MSA stream has been "purified", by some processing unit or device, if and when the output stream is more pure, in any significant way, then the input stream, regardless of how great or how little the improvement or increased level of purity might be.

On a practical and realistic level, except in very rare situations, no well-run company is going to pay to build and run a "purification" unit, unless it provides a substantial improvement in purity, which makes the "purified" output worth the additional costs. Accordingly, even though any number of purification procedures which work well, on quantities of liquid measured in milliliters or less, might theoretically be able to create a "purified" preparation in industrial volumes, they do not offer serious candidates for consideration unless they can indeed be scaled up to very large volumes.

By far the most commonly used purification process for handling the volumes of oil, gas, and petrochemicals that are processed and purified every day is distillation. Very briefly, industrial-scale continuous-flow distillation usually involves maintaining a vertical enclosed tower, with multiple "trays" or "levels" inside it at different heights, at a range of different temperatures, arrayed from top to bottom (usually with the hottest temperatures at the top; any other system requires active heat control and increased operating expenses). By using any of several types of non-linear flow channels (often called baffles, bubblers, bubble caps, or similar terms) that pass through generally horizontal "trays" (or plates, etc.), a volatile liquid of interest can processed in a way that will cause most of a specific desired compound to either: (i) condense, and gather in liquid form, on a specific tray which is maintained at a specific temperature, inside the tower (or on a limited number of trays adjacent to each other, clustered together in a limited vertical zone, all operating within a limited temperature range); or, (ii) emerge from the tower, in relatively pure gaseous form, at a specific location in the tower, if the tower is operated at vacuum conditions. The targeted liquid or gas is collected, in relatively pure (distilled) form, by (i) draining off any and all liquid which has accumulated on the specific distillation tray(s) which operates at the temperature where that compound will condense from a gas, into a liquid, or (ii) suctioning out vapors which accumulate at a specific exit point on the tower.

Since MSA will have a distinctly different boiling/condensation temperature than any other compound in a "rich acid" stream being processed by a system as shown in FIG. 1 (exact temperatures will vary, depending mainly on the operating pressure inside a specific distillation tower), distillation offers a direct and straightforward approach to an effective MSA extraction step. If properly run, using a well-designed and properly-sized tower (exact dimensions will depend on flow rates and other parameters, at any specific manufacturing site), even single-step distillation (without using any of numerous candidate enhancements that are known) can very likely reach or exceed 99% purity levels, even at high flow rates. If "candidate enhancements" are used (which will add to processing costs), even higher purity levels can be achieved, by distillation.

Unless and until results from pilot plant tests indicate otherwise, the available scientific data on MSA, and computer simulations that have been run on industry-standard distillation modeling software, indicate that MSA can be separated from sulfuric acid, under a vacuum of about 10 to 100 mbar (i.e., from 1/10 to 1/100 atmospheric pressure), and at a temperature of about 185-215° C. The MSA vapor will leave the side of distillation column 744 via line 745, and can be transported to a condenser which will condense the vapors into a high purity liquid at close to a concentration of 100%, which can be sold in concentrated form, or which can be diluted to a lower concentration (such as 70%) by water or other suitable solvent.

It also should be noted that various other types of separation methods and approaches are used to handle industrial-scale separations and purifications, and any such methods can be evaluated for use to extract MSA from a "rich acid" stream which also contains sulfuric acid, using no more than routine testing, which often will be carried out at no charge by a vendor company which hopes to sell the type of processing equipment it will offer to test.

For example, various types of "membrane filtration" are used industrially, most commonly by pumping a liquid or gas at high pressure into a large and long metal cylindrical "shell" which contains dozens, hundreds, or thousands of thin tubes made of a much smaller hollow strands of a selected semi-porous polymer, packed lengthwise inside the shell. If the compound of interest is able to pass through the specific type of porous polymer that has been selected for that use, it can move from one zone inside the shell (such as the interiors of the polymeric tubes), into a different zone (such as the interstitial gaps between the polymer tubes). This allows the emergent gas or liquid to be separated into two different streams; one stream will contain molecules which passed through the walls of the semi-porous polymer tubes, and the other stream will contain molecules which could not pass through that polymer.

Other types of membrane separation also are known, and some are used at industrial scales. Unfortunately, a variety of terms have been created to distinguish between them, and since these terms are often created, guided, and used mainly by companies and sales agents that want to sell one particular type of equipment while discouraging the use of other types, these terms are not always used consistently, or with clear boundaries between them. Such terms include reverse osmosis, forward osmosis, electrodialysis reversal, nanofiltration, and membrane distillation. Companies that sell any of these types of processing equipment can be readily located; they can explain the exact differences between those terms (as they choose to interpret and apply those terms), and they can assist in testing MSA/sulfuric acid mixtures, using whatever equipment they sell, to obtain reliable information about how much an appropriately-sized unit will cost for any specific manufacturing site, and how long those types of membranes will last, when used to handle a mixture of not just one but two strong acids.

In addition, there are still other types of separation and purification methods that may be useful for removing MSA from a sulfuric acid mixture, other than distillation and membrane-using methods. Such methods include:

(i) pressure swing adsorption, which generally works better with gases than with liquids, and which usually requires different components in a mixture to "adsorb" (i.e., cling to a solid surface) at different rates or affinity levels on relatively expensive materials, such as zeolites, activated carbon, or molecular sieves; and, (ii) cryogenic methods, which generally involve temperatures low enough to separate materials based on behaviors or properties which different components exhibit when they become cold; for example, many carbon-containing compounds become waxy and sticky when they become cold, allowing them to clink tightly to a screen or similar surface, which can then be used to remove them from a liquid mixture, allowing the waxy compound to be released from the screen or other surface, by simply heating it up again.

Accordingly, any of these purification methods (or any other candidate methods, already known or hereafter discovered, which have been shown to be effective in large-volume manufacturing operations) can be evaluated for use for removing MSA from a mixed stream of MSA and sulfuric acid, in an MSA extraction unit 130 as shown in FIG. 1.

The net effect of any such "MSA extraction unit" is fairly simple and straightforward: it will divide a "rich acid" stream (i.e., which has emerged from MSA-forming reactor 110, and which therefore carries a relatively high concentration of MSA, and some fixed (and presumably substantially lower) quantity/concentration of sulfuric acid, into two separate and distinct output streams:

(i) a first stream of "purified" MSA, with a very high concentration of MSA (in most cases of interest, this purified stream is likely to have at least about 98% purity, and in many cases it will be even higher), with very little (and preferably no) sulfuric acid content; and (ii) a second stream, referred to herein as a "spent acid" stream, as discussed below.

"Spent Acid" and "the Acid Loop"

As described directly above, the "second" stream which emerges from the MSA extraction unit 130 is called a "spent acid" stream. A large fraction (in most cases, a VERY large majority, such as more than 90%) of the valuable and desired component (i.e., the MSA) will have been removed from that "spent acid" stream, by the time it emerges from the MSA extraction unit 130. It remains highly acidic, since its main component will be concentrated sulfuric acid; however, it falls squarely within the chemical use of the term "spent", because it has already done its desired and intended job, and now it needs to be handled and processed, somehow.

As a brief side note, this "spent acid" stream could also be called a "reduced" stream; however, the term "reduced", when used in chemistry, has other, inconsistent meanings, which relate to electron density, electrical/ionic charges, and valence states. Therefore, the term "spent acid" is preferred and used herein, to refer to an MSA stream from which most of the MSA has been removed.

Unless and until specific results from pilot plant testing indicate otherwise, it is presumed to be advisable to leave some portion of the MSA, from the "rich acid" stream, in the "spent acid" stream. This arises from two factors: (i) it becomes much more expensive to drive any type of chemical manufacturing process to an absolute 100% level of completion, compared to allowing it to reach some reasonable and appropriate level and then moving on; and, (ii) the methyl domain of MSA helps in its solvent activity, by making it easier for fresh methane molecules to be driven into a liquid solvent that contains a substantial MSA content.

Accordingly, as shown in FIG. 1, the "spent acid" stream from MSA extraction unit 130 will be kept within circulating, within the overall integrated system 100, as a valuable component of that system, and, since that approach is being taken, it should be pointed out that a continuously-flowing "acid loop" (as indicated by the components directly above the bracket, on the bottom of FIG. 1) has been designed as an integral part of this processing system. The complete "acid loop" includes:

(i) a "rich acid" portion, which emerges as the "high MSA" "rich acid" mixture from MSA-forming reactor 110, and travels through evaporator 120, to reach MSA extraction unit 130; and, (ii) a "spent acid" portion, which emerges from the MSA extraction unit 130, and which is pumped back into the MSA-forming reactor 110.

If desired, the "spent acid" stream can be passed through a purification unit 140, which can perform any desired and useful type of procedure on the spent acid stream before it is returned to the MSA-forming reactor 110. As just one example, since SO2 molecules are known to be highly undesirable chain terminators inside the MSA-forming reactor 110, purification unit 140 can be used to oxidize any SO2 molecules, and boost them back up to SO3 molecules, before the spent acid is returned to the MSA-forming reactor 110.

This, there has been shown and described a complete and integrated chemical processing system for making MSA in high yields, by (i) using a radical chain reaction to combine methane with sulfur trioxide, and then (ii) using known types of chemical processing components, assembled in a new and useful way, to treat the "rich acid" stream which will emerge from that reactor.

The invention claimed is:

1. A method for manufacturing methane-sulfonic acid (MSA) which integrates sulfonation chemistry and selective extraction, to combine methane and sulfur trioxide in a manner which converts them into MSA having purity greater than 90 percent, comprising the following steps:

a. sulfonating methane (CH4) with sulfur trioxide (SO3) in an MSA-forming reactor, by using a radical chain reaction which forms MSA in an acidic media which also contains sulfuric acid, thereby creating a rich acid mixture which contains (i) an enriched concentration of MSA compared to sulfuric acid, and (ii) substantial quantities of unreacted CH4 and SO3;

b. processing said rich acid mixture by removing at least a portion of said unreacted CH4 and SO3 from said rich acid mixture;

c. processing said rich acid mixture in an MSA extraction processor, in a manner which extracts a majority portion of the MSA from said rich acid mixture, thereby forming a first outlet stream containing a purified MSA liquid product, and a second outlet stream containing a spent acid mixture having a reduced quantity of MSA mixed with sulfuric acid;

d. recycling said spent acid mixture back into said MSA-forming reactor for mixing with additional CH4 and SO3 in said MSA-forming reactor.

2. The method of claim 1 wherein said unreacted CH4 and SO3, which were removed from said rich acid mixture, are returned to said MSA-forming reactor.

3. The method of claim 1 wherein the rich acid mixture is processed by passing it continuously through an evaporator to reduce the pressure to a lower pressure close to ambient and flash off a portion of the unreacted SO3 and dissolved methane in the rich acid mixture.

4. The method of claim 3 wherein the flashed portion of unreacted SO3-methane gas mixture is fed to a condenser where the SO3 is condensed to a liquid for return to the MSA-forming reactor.

5. The method of claim 1 wherein the MSA extraction processer in which the rich acid mixture in step c is processed is a distillation unit.

6. The method of claim 5 wherein the distillation unit operates under a vacuum at a temperature of about 185° C.-215° C.

7. The method of claim 1 wherein the SO3 in the MSA-forming reactor in step a is in the gamma liquid form.

* * * * *